US006971873B2

(12) United States Patent
Sachdeva et al.

(10) Patent No.: US 6,971,873 B2
(45) Date of Patent: *Dec. 6, 2005

(54) VIRTUAL BRACKET LIBRARY AND USES THEREOF IN ORTHODONTIC TREATMENT PLANNING

(75) Inventors: Rohit Sachdeva, Plano, TX (US); Rüdger Rubbert, Berlin (DE); Thomas Weise, Berlin (DE)

(73) Assignee: OraMetrix, Inc., Richardson, TX (US)

( * ) Notice: Subject to any disclaimer, the term of this patent is extended or adjusted under 35 U.S.C. 154(b) by 160 days.

This patent is subject to a terminal disclaimer.

(21) Appl. No.: 10/137,523

(22) Filed: May 1, 2002

(65) Prior Publication Data

US 2002/0156652 A1 Oct. 24, 2002

Related U.S. Application Data

(63) Continuation-in-part of application No. 09/835,039, filed on Apr. 13, 2001, now Pat. No. 6,648,640, and a continuation-in-part of application No. 09/560,127, filed on Apr. 28, 2000, now Pat. No. 6,554,613, and a continuation-in-part of application No. 09/552,190, filed on Apr. 19, 2000, now abandoned.

(51) Int. Cl.[7] ............................................... A61C 3/00
(52) U.S. Cl. ....................................... 433/24; 433/213
(58) Field of Search ................................... 433/24, 213

(56) References Cited

U.S. PATENT DOCUMENTS

| | | | |
|---|---|---|---|
| 4,656,860 A | | 4/1987 | Orthuber et al. |
| 5,273,429 A | | 12/1993 | Rekow et al. ............... 433/215 |
| 5,291,771 A | * | 3/1994 | Tomo et al. .................... 72/306 |
| 5,338,198 A | | 8/1994 | Wu et al. .................... 433/213 |
| 5,395,238 A | | 3/1995 | Andreiko et al. .............. 433/24 |
| 5,431,562 A | | 7/1995 | Andreiko et al. .............. 433/24 |
| 5,454,717 A | | 10/1995 | Andreiko et al. .............. 433/24 |
| 5,474,448 A | | 12/1995 | Andreiko et al. .............. 433/24 |
| RE35,169 E | | 3/1996 | Lemchen et al. .............. 433/24 |
| 5,518,397 A | | 5/1996 | Andreiko et al. .............. 433/24 |
| 5,533,895 A | | 7/1996 | Andreiko et al. .............. 433/24 |
| 5,683,243 A | | 11/1997 | Andreiko et al. ............... 433/3 |

(Continued)

FOREIGN PATENT DOCUMENTS

WO      WO0180761      11/2001

*Primary Examiner*—John J Wilson
(74) *Attorney, Agent, or Firm*—McDonell Boehnen Hulbert & Berghoff LLP

(57) ABSTRACT

An orthodontic workstation stores a library of virtual three-dimensional brackets in a memory. Each of the virtual brackets has a unique three-dimensional configuration and prescription. Typically, the library of bracket comprises a library of commercially available, off-the-shelf brackets. The workstation further includes an interactive treatment planning program that permits a user to move teeth from a virtual model of the dentition to a proposed set-up. In one possible embodiment, the treatment planning program provides the ability to display a virtual bracket placed on a virtual tooth and change the prescription or configuration of the virtual bracket. The treatment program automatically compares the modified prescription with the prescription information of the virtual brackets in the library and selects a bracket from the library that most closely matches the virtual bracket displayed on the tooth. Thus, the user does not have to use customized brackets. Any deviation in tooth position resulting from a discrepancy between the off-the-shelf bracket and the user-defined bracket can be corrected for by changing the position of the bracket on the tooth or by changing the shape of the archwire.

15 Claims, 6 Drawing Sheets

U.S. PATENT DOCUMENTS

| | | |
|---|---|---|
| 5,879,158 A | 3/1999 | Doyle et al. .................. 433/24 |
| 6,068,482 A | 5/2000 | Snow ........................ 433/223 |
| 6,123,544 A * | 9/2000 | Cleary ........................ 433/24 |
| 6,210,162 B1 | 4/2001 | Chishti et al. ............... 433/213 |
| 6,217,325 B1 | 4/2001 | Chishti et al. ................ 433/24 |
| 6,227,850 B1 | 5/2001 | Chishti et al. ................ 433/24 |
| 6,315,553 B1 | 11/2001 | Sachdeva et al. ............. 433/24 |
| 6,318,995 B1 | 11/2001 | Sachdeva et al. ............. 433/24 |
| 6,350,120 B1 | 2/2002 | Sachdeva et al. ............. 433/24 |
| 6,464,496 B1 | 10/2002 | Sachdeva et al. ............. 433/24 |
| 6,471,512 B1 | 10/2002 | Sachdeva et al. ............. 433/24 |
| 6,632,089 B2 * | 10/2003 | Rubbert et al. ............... 433/24 |
| 6,733,289 B2 * | 5/2004 | Manemann et al. .......... 433/24 |
| 6,736,638 B1 | 5/2004 | Sachdeva et al. |
| 2002/0025503 A1 * | 2/2002 | Chapoulaud et al. ......... 433/24 |
| 2002/0028417 A1 | 3/2002 | Chapoulaud et al. ......... 433/24 |

* cited by examiner

VIRTUAL BRACKET LIBRARY AND USES THEREOF IN ORTHODONTIC TREATMENT PLANNING

CROSS-REFERENCE TO RELATED APPLICATION

This is a continuation in part of the U.S. patent application Ser. No. 09/835,039 filed Apr. 13, 2001, now issued as U.S. Pat. No. 6,648,640, the entire content of which is incorporated by reference herein. This is also a continuation in part of the U.S. patent application Ser. No. 09/560,127 filed Apr. 28, 2000, now issued as U.S. Pat. No. 6,554,613, and a continuation in part of the U.S. patent application Ser. No. 09/552,190 filed Apr. 19, 2000, now abandoned, the contents of both of which are incorporated by reference herein.

BACKGROUND OF THE INVENTION

A. Field of the Invention

This invention relates generally to the fields of orthodontics. More particularly, the invention relates to a computer-based method of selecting one or more brackets to use with an orthodontic patient, and a library of virtual brackets stored in a computer for use in conjunction with planning treatment for the patient.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored. The orthodontist makes corrections to the bracket position and/or wire shape manually.

The key to efficiency in treatment and maximum quality in results is a realistic simulation of the treatment process. Today's orthodontists have the possibility of taking plaster models of the upper and lower jaw, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per jaw that covers all brackets and relevant portions of every tooth. Using such a transfer tray guarantees a very quick and yet precise bonding using indirect bonding.

However, it is obvious that such an approach requires an extreme amount of time and labor and thus is too costly, and this is the reason why it is not practiced widely. The normal orthodontist does not fabricate set-ups; he places the brackets directly on the patient's teeth to the best of his knowledge, uses an off-the-shelf wire and hopes for the best. There is no way to confirm whether the brackets are placed correctly; and misplacement of the bracket will change the direction and/or magnitude of the forces imparted on the teeth. While at the beginning of treatment things generally run well as all teeth start to move at least into the right direction, at the end of treatment a lot of time is lost by adaptations and corrections required due to the fact that the end result has not been properly planned at any point of time. For the orthodontist this is still preferable over the lab process described above, as the efforts for the lab process would still exceed the efforts that he has to put in during treatment. And the patient has no choice and does not know that treatment time could be significantly reduced if proper planning was done.

U.S. Pat. No. 5,431,562 to Andreiko et al. describes a computerized, appliance-driven approach to orthodontics. In this method, certain shape information of teeth is acquired. A uniplanar target archform is calculated from the shape information. The shape of customized bracket slots, the bracket base, and the shape of an orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

Other patents of interest include Lemchen et al., Reissue Patent No. 35,169, and the following patents, all to Andreiko et al.: U.S. Pat. No. 5,431,562; U.S. Pat. No. 5,683,243; U.S. Pat. No. 5,518,397; U.S. Pat. No. 5,454,717; U.S. Pat. No. 5,395,238; U.S. Pat. No. 5,474,448, and U.S. Pat. No. 5,553,895.

More recently, in the late 1990's Align Technologies began offering transparent, removable aligning devices as a new treatment modality in orthodontics. In this system, a plaster model of the dentition of the patent is obtained by the orthodontist and shipped to a remote appliance manufacturing center, where it is scanned with a laser. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position. Representative patents describing the Align process include U.S. Pat. Nos. 6,217,325; 6,210,162; and 6,227,850.

Other patents addressed to planning treatment for a patient include Doyle, U.S. Pat. No. 5,879,158, Wu et al., U.S. Pat. No. 5,338,198 and Snow et al., U.S. Pat. No. 6,068,482.

SUMMARY OF THE INVENTION

In a first aspect, a workstation for orthodontic treatment planning is provided. The workstation includes a central processing unit and a memory. The memory stores a library of virtual three-dimensional brackets, each of the brackets in the library having a unique prescription, i.e., physical configuration such as slot depth, slot angle, wing configuration, hook shape or configuration, etc. Typically, the virtual brackets in the library are three-dimensional representations of off-the-shelf brackets commercially available from vendors of such brackets. The library can be created either through CAD models of the brackets, obtained from the manufacturers, or created from scratch from scanning a set of brackets with a three-dimensional scanner, converting the scan data to three-dimensional virtual objects, and storing the objects in the memory along with the published prescription data for the bracket.

One example of the use of the library of virtual there-dimensional brackets is planning treatment of an orthodontic patient using the workstation. The memory of the workstation stores an interactive treatment planning program and a three-dimensional virtual model of the dentition of a patient. The treatment-planning program allows the user to select a virtual three-dimensional bracket from the library for a virtual tooth in the three-dimensional virtual model of the dentition. Another example of its use is a situation where the user places a virtual bracket on the tooth, and modifies the prescription of the bracket in order to change tooth position. Rather than requiring the user to have a customized bracket manufactured for the user in accordance with the modified prescription, the treatment-planning program can search through the library for a bracket that most closely matches the modified prescription bracket. The bracket from the library is then presented to the user and placed on the virtual tooth for evaluation.

Thus, in one possible implementation the workstation includes a set of instructions that performs the operation of selecting a virtual bracket from the library based on a comparison of the modification of the prescription made by the user on the user interface and the prescription (i.e, configuration) of the virtual brackets stored in the library.

In another aspect, the treatment planning program preferably includes a set of instructions that provides for a display of a virtual tooth in the virtual model of the dentition and a virtual bracket placed on tooth. Ideally, the display further comprises a display of a prescription of the virtual bracket that is placed on the tooth and allows the user to vary the prescription. Preferably, changes to the bracket prescription by the user are immediately carried into effect on the user interface. Since the virtual bracket is virtual bonded or attached to the tooth, changes in bracket prescription (e/g. slot angle) will result in a change in the position of the tooth. This feature allows the user to change the position of a tooth in the virtual model simply by changing the bracket prescription.

In another aspect, a method of planning treatment for an orthodontic patient is provided. The method comprises the steps of:

a) obtaining a three-dimensional virtual model of the dentition of said patient;

b) storing said virtual model of the dentition in a memory associated with an orthodontic treatment planning workstation;

c) providing, in the workstation, an interactive orthodontic treatment planning program enabling a user to 1) move the teeth in said virtual model to a proposed finish position and 2) place a virtual three-dimensional bracket on a virtual tooth in the virtual model;

d) providing, in said treatment planning program, an ability of a user to define the prescription of the virtual bracket; and e) automatically selecting an off-the-shelf bracket for the virtual bracket.

For example, the step e) of selection of the bracket can be made by comparing the user-specified bracket prescription with the prescription of the brackets in the library and selecting the bracket that most closely matches the user specification of the brackets.

In another aspect, a method of planning treatment for an orthodontic patient is provided. The method comprises the steps of:

a) obtaining a three-dimensional virtual model of the dentition of the patient;

b) storing the virtual model of the dentition in a memory associated with an orthodontic treatment planning workstation;

c) providing, in the workstation, an interactive orthodontic treatment planning program enabling a user to move the teeth in the virtual model to a proposed finish position;

d) providing, in the memory, a library of virtual, three-dimensional brackets; and e) providing in the treatment planning program an ability of a user to select an individual bracket from the library and place the individual bracket on a virtual tooth in the virtual model.

These and other aspects and features of present invention will be more fully explained in the following detailed description of a presently preferred embodiment of the invention.

BRIEF DESCRIPTION OF THE DRAWINGS

Presently preferred embodiments of the invention are described below in conjunction with the appended drawing figures, where like reference numerals refer to like elements in the various views, and wherein.

DETAILED DESCRIPTION OF PREFERRED EMBODIMENTS

Figure 1:
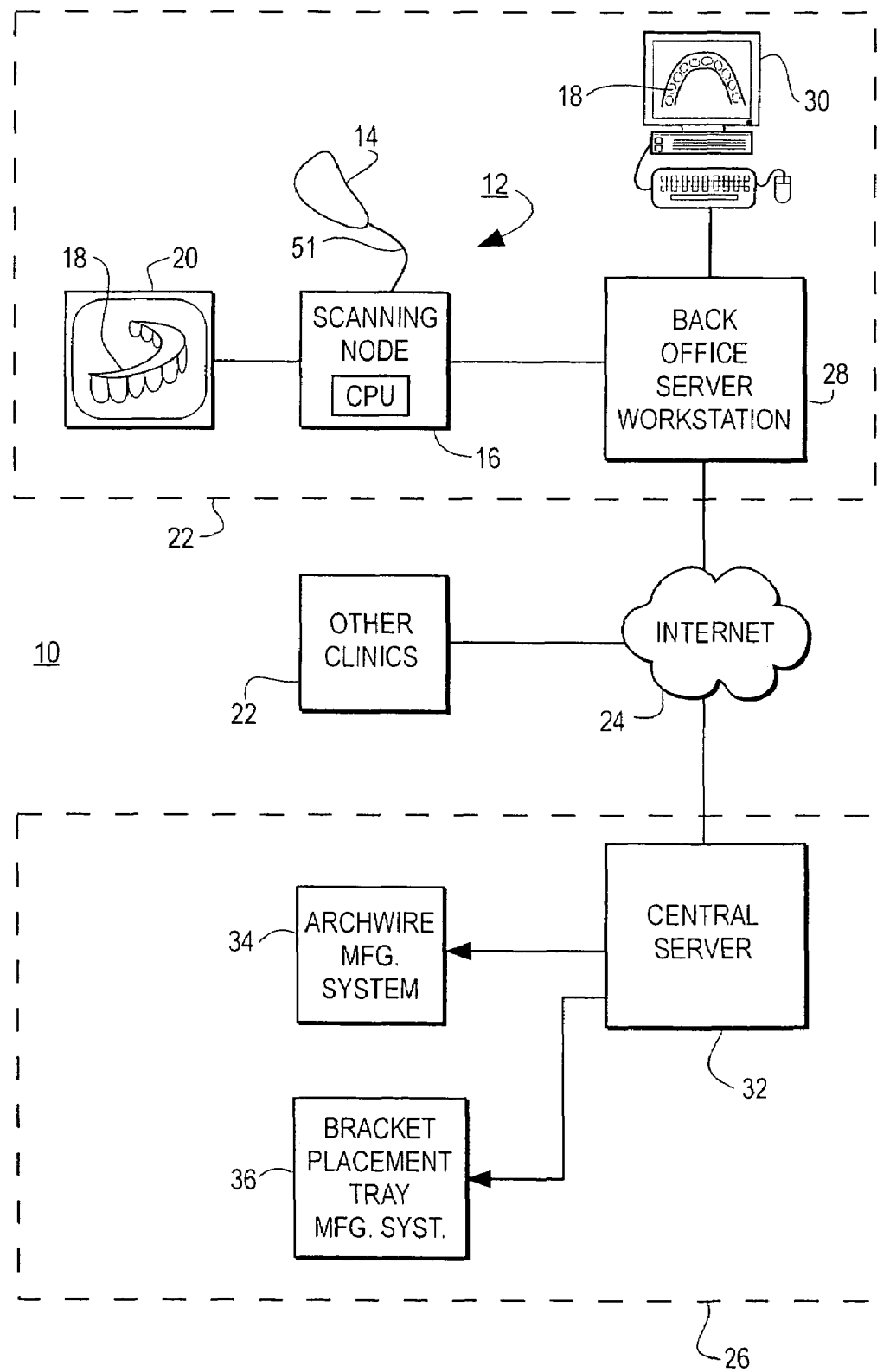
FIG. 1 is an illustration of an orthodontic care system incorporating a hand-held scanner system and treatment planning software in accordance with a representative embodiment of the invention. The hand-held scanner is used by the orthodontist to acquire three-dimensional information of the dentition and associated anatomical structures of a patient and provide a base of information for interactive, computer software-based diagnosis, appliance design, and treatment planning for the patient. The scanner is suitable for in-vivo scanning, scanning a plaster model, scanning an impression, or any combination thereof.

Before describing in detail a virtual bracket library in accordance with the present invention and its uses in planning orthodontic treatment, further background information on a representative treatment planning program and one possible technique for generation of a virtual model of the dentition will be provided first. It will be appreciated that that present invention is applicable to other types of treatment planning software and other techniques for generation of a virtual model of the patient's dentition. Hence, the following description is provided for purposes of illustration and explanation of the best mode contemplated for practicing the invention, and the scope of the invention is not limited thereby The selection of a bracket for use in treatment of a patient and the use of a library of virtual brackets in planning treatment of an orthodontic patient in accordance with a preferred embodiment of the invention makes use of three-dimensional virtual models of teeth. The virtual models of teeth are stored in a memory and available to a general-purpose computer, such as a computer configured with software to function as an orthodontic workstation. Virtual models of teeth of a patient can be obtained by using a laser scanner to scan a physical model of the dentition. Alternatively, the teeth can be scanned in vivo, or a model of the dentition can be scanned, by a hand-held three-dimensional optical scanner such as the type described in the published PCT application of OraMetrix, Inc., PCT/US01/11969, publication no. WO 01/80761, the entire contents of which is incorporated by reference herein.

Once the teeth have been scanned, the three-dimensional scan data can be represented in a computer and displayed to the user on a user interface as a three-dimensional model. There are a variety of techniques known in the CAD/CAM art for representing a three-dimensional surface, and the choice of a particular technique or format for representation of the virtual teeth is not particularly important. The present invention will be described in context of a representation of a surface as a set of points that define contiguous three-dimensional triangular shaped surface segments.

After the dentition, or a physical model of the dentition, has been scanned, it is helpful to separate the individual teeth from the rest of the anatomical structures (e.g., gingival tissue) so that individual teeth can be represented as independently moveable, individual three-dimensional virtual objects. This is described in the above-referenced PCT application of OraMetrix. Once the teeth have been separated into such individual objects, computer-aided design and computer-aided manufacturing (CAD/CAM) techniques can be used to move the teeth relative to each other to arrive at a proposed set-up for treatment of the patient. A particularly advanced and highly preferred treatment planning software application that performs these and other tasks is described at length in the above-referenced PCT application of OraMetrix. The software preferably provides the user with the ability to display the arches individually, or together, either alone or in an occluded condition. The relative position of the arches in the occluded position is preferably user-specified by the treatment planning software. Since the techniques used to moved teeth and/or arches relative to each other are already described in the patent literature, the details are omitted from the present discussion for the sake of brevity.

Whereas in the prior art Andreiko et al. patents the treatment goals and appliance design were mathematically derived from measurements of the malocclusion, with little or no user involvement, the preferred embodiment provides for an interactive treatment planning system in which the tools are provided to the orthodontist to play an active role in diagnosis, treatment planning and appliance design. For example, the orthodontist can change the configuration for the archform, can correct individual tooth positions on the archform on a tooth by tooth basis, change the bracket position on the teeth, and can add additional bends in the archwire.

In the illustrated embodiment, the treatment planning system also uses three-dimensional objects comprising virtual models of orthodontic appliances, such as brackets and orthodontic archwires. Preferably, a library comprising a collection of individual, unique, commercially available off-the-shelf brackets is stored in the memory of the workstation. The brackets are stored as individual three-dimensional virtual objects. The bracket models can be obtained as CAD models from bracket manufacturers, or from a scanning of the brackets themselves. The wire models can be derived from the cross-sectional shape and length of the wire, and parameters as to the shape of an arch that the wire is representing. Obviously, in other types of orthodontic treatment scenarios where brackets are not used, other types of virtual three-dimensional objects may be used, such as retainers, Herbst appliances, expansion devices, the substantially transparent, removable aligning devices commercialized by Align Technologies, etc. In a preferred embodiment, these virtual appliance objects are stored in a memory accessible to the orthodontic treatment planning workstation, such as in the workstation's hard disk memory.

The treatment planning that will be performed by the user for a given patient will necessarily vary from patient to patient. The preferred embodiment of the treatment planning method provides a wealth of viewing, measuring, and simulation tools by which the orthodontist can plan treatment for any given patient. For ease of understanding and clarity, the treatment planning software will be mainly described below in terms of screen displays that are displayed on a user interface and the key functionality in the screen displays. A person skilled in the art will be able to program a computer to provide these functions from the present description and representative screen displays.

It is contemplated that most if not all aspects of the treatment planning software will ordinarily be installed on a back office server or workstation in an orthodontic clinic. The software may also be located in other clinics of related specialties, such as periodontal clinics, family dental clinics, and clinics of oral surgeons, so that the treatment planning, patient virtual model, and other parameters can be shared amongst multiple users. Some functionality of the software may not be available or used where the software is distributed among multiple specialties. For example, the periodontist may not have any desire to change or modify tooth position or archwire shape. To facilitate interaction regarding the patient at clinics of various specialties, it is desirable to equip each clinic or office with the scanning system described herein (or other suitable scanner), for treatment monitoring purposes, and so that when a new patient arrives at any of the clinics they can be scanned and the digital model shared with other specialties.

It is possible that some or all of the treatment planning software could be installed at a remote site and some or all of the treatment planning done remotely, e.g, by a central service center, by a remotely located orthodontist, or by a precision appliance service center as described below. In this latter scenario, the three-dimensional model of the malocclusion and necessary patient information is transmitted over a suitable communications link (e.g. the Internet) to the remote location. An orthodontist or other trained person operating the software at the remote location separates the teeth from the surrounding anatomical structures to create a set of independent tooth objects, studies the malocclusion and the treatment objectives for the patient, and uses the software to arrive at an initial proposed target situation for the patient. The initial proposed target situation is sent back to the orthodontist for review, modification, and/or approval. The model can be reviewed simultaneously and interactively with the patient, or shared with other specialists, or with a precision appliance manufacturing center.

To carry this out, a copy of the digital model of the target situation (or of the malocclusion) is maintained on a central server at one location, such as the remotely located precision appliance manufacturing center. The users access that copy of the model over the Internet and manipulates it using the treatment planning software described herein. All users that simultaneously participate in interactive, simultaneous manipulation of the model view the same thing. The copy of the model that is stored in the orthodontist's office remains unchanged.

FIG. 1 is an illustration of a representative orthodontic care system 10 in which the invention may be practiced. The system includes a scanner system 12. The scanner system 12 includes a hand-held scanner 14 that is used by the orthodontist to acquire three-dimensional information of the dentition and associated anatomical structures of a patient. The scan data is processed in a scanning node or workstation 16 having a central processing unit, such as a general-purpose computer. The scanning node 16, either alone or in combination with a back-office server 28, generates a three-dimensional virtual computer model 18 of the dentition. The computer model provides the orthodontist and the treatment planning software with a base of information to plan treatment for the patient. The model 18 is displayed to the user on a monitor 20 connected to the scanning node 16.

The illustrated orthodontic care system consists of a plurality of orthodontic clinics 22 which are linked via the Internet or other suitable communications medium 24 (such as the public switched telephone network, cable network, etc.) to a precision appliance service center 26. Each clinic 22 has a back office server work station 28 having its own user interface, including a monitor 30. The back office server 28 executes an orthodontic treatment planning software program, described at length below. The software obtains the three-dimensional digital data of the patient's teeth from the scanning node and displays the model 18 for the orthodontist. The treatment planning software includes features to enable the orthodontist to manipulate the model 18 to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models, modify the prescription of the virtual brackets, automatically select an off-the-shelf bracket that most closely matches the modified bracket, and design a customized archwire for the patient given the selected bracket position. When the orthodontist has finished designing the orthodontic appliance for the patient, digital information regarding the patient, the malocclusion, and a desired treatment plan for the patient are sent over the communications medium to the appliance service center 26. A customized orthodontic archwire and a device for placement of the brackets on the teeth at the selected location is manufactured at the service center and shipped to the clinic 22.

As shown in FIG. 1, the precision appliance service center 26 includes a central server 32, an archwire manufacturing system 34 and a bracket placement manufacturing system 36. These details are not particularly important to the treatment panning methods and apparatus and are therefore omitted from the present discussion for sake of brevity. For more details on these aspects of the illustrated orthodontic care system, the interested reader is directed to the patent application of Rudger Rubbert et al., filed on Apr. 13, 2001, entitled INTERACTIVE AND ARCHWIRE-BASED ORTHODONTIC CARE SYSTEM BASED ON INTRA-ORAL SCANNING OF TEETH, Ser. No. 09/835,039, now issued as U.S. Pat. No. 6,648,640, the contents of which are incorporated by reference herein.

The detailed operation of the scanner system and method for acquiring the three-dimensional model of the dentition is described at length in the Rubbert et al. patent application and in the published PCT application of OraMetrix, Inc. cited previously, therefore a further more detailed discussion is omitted for the sake of brevity.

Basically, during operation of the scanner to scan an object of unknown surface configuration, hundreds or thousands of images are generated of the projection pattern as reflected off of the object in rapid succession. For each image, pixel locations for specific portions, i.e., points, of the reflected pattern are compared to entries in the calibration table. X, Y and Z coordinates (i.e., three dimensional coordinates) are obtained for each of these specific portions of the reflected pattern. For each picture, the sum total of all of these X, Y and Z coordinates for specific points in the reflected pattern comprise a three-dimensional "frame" or virtual model of the object. When hundreds or thousands of images of the object are obtained from different perspectives, as the scanner is moved relative to the object, the system generates hundreds or thousands of these frames. These frames are then registered to each other to thereby generate a complete and highly accurate three-dimensional model of the object, here the patient's teeth. The process can be done in vivo or from a physical model of the dentition.

At noted above, the treatment planning features are applicable to a three-dimensional model of the dentition derived from any source, including CAT scans, laser scans taken from dental impressions, models or otherwise, and ultrasound. The hand-held optical scanner described herein offers numerous advantages, particularly it allows scans to be obtained in real time very quickly, i.e., in a matter of minutes. The scans can be taken fully from the mouth or from a model, or from some combination of the two.

After the three-dimensional model of the upper and lower arch is obtained, the teeth in the model are virtually extracted from the surrounding anatomical structures and represented as individual three-dimensional tooth objects. A presently preferred method of carrying this out is described in the published PCT application of OraMetrix, Inc. cited previously. The tooth separation process allows individual virtual teeth to be moved independently in three dimensions on the computer in an interactive, user-specified manner, since they are individual three-dimensional objects. The separation process described below has one further advantage, namely requiring less memory to represent an individual tooth. Consequently, the treatment planning software can process treatment planning steps for the teeth more quickly.

Initial Virtual Bracket Placement

With the individual teeth now cut from the three-dimensional model of the dentition and represented as tooth objects, they can be moved relative to each other in three dimensions. Since orthodontics assumes that a bracket is fixedly bonded to a tooth, by moving the bracket one moves the tooth. The next step in the process is thus selecting an initial location to bond the brackets to the tooth. As noted below, this initial location can be adjusted by the user operating the treatment planning software. The spatial location of the surfaces of the bracket and the surfaces of the corresponding tooth are known. Collision avoidance algorithms are used to keep the bracket positioned on the surface of the tooth and prevent the virtual bracket from entering the tooth itself, a clinically undesirable result. The user is able to move the bracket independently of the tooth by activating an icon (such as one shaped like a magnet to signify the mating of the bracket to the tooth). When the bracket is moved to the new location, the tooth matches up to the surface of the bracket.

The brackets are represented in the software as virtual three-dimensional objects, and the surface of all the brackets and the teeth are known in three dimensional spatial coordinates. Accordingly, collision detection algorithms are employed to detect when simulated tooth or bracket movement would result in a collision between brackets and teeth. Similar collision algorithms are provided to prevent the adhesion surface of the bracket from migrating into the body of the virtual tooth object and to keep the brackets located on the surface of the teeth. If the user wishes to move the location of the brackets, the movement of the teeth follows the movement of the bracket. Also, again since the bracket is a three-dimensional virtual object with known spatial coordinates, the user is provided with a tool (such as an icon) which when activated allows the user to move the bracket about one plane or axis, and freeze the movement in the other directions.

Figure 2:
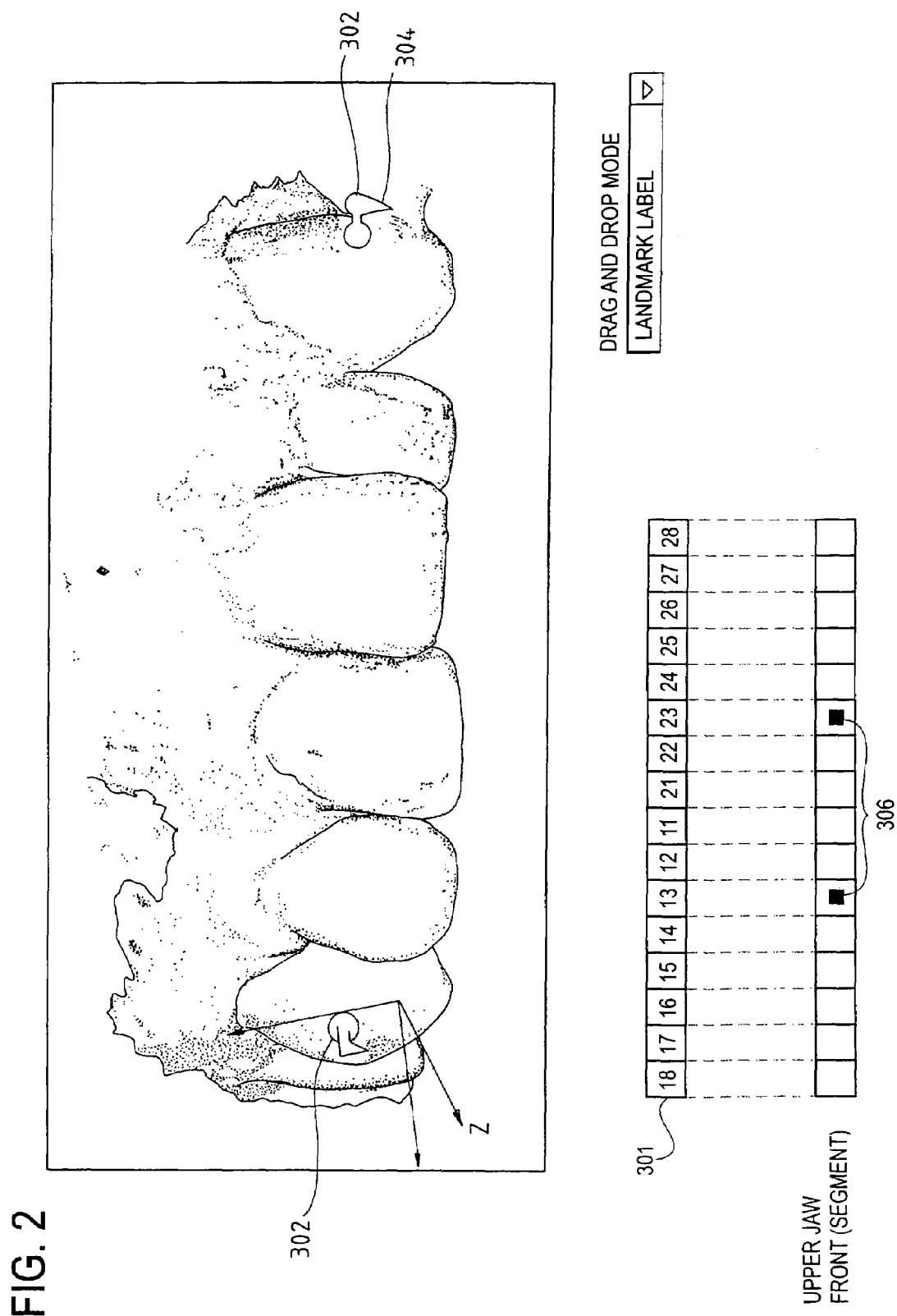
FIG. 2 is a screen shot displayed on the display of the back office server of FIG. 1, showing a graphical representation of a three-dimensional model of a patient's upper front teeth. The user is applying landmarks to the teeth as a preliminary step in determining bracket placement on the labial surface of the teeth.

One method of initial virtual bracket placement uses landmarks, which are icons placed by the user on the surface of the virtual teeth indicating the position at which the bracket is to be bonded to the tooth. Landmarks 302 such as shown in FIG. 2 are placed on the labial surfaces of all the teeth. The landmarks are placed at the location where the orthodontist expects to place an orthodontic bracket to correct the malocclusion. The bracket shape is shown on the monitor. Three-dimensional templates for a variety of commercially available brackets are stored in memory and the software asks the orthodontist to select a particular manufacturer and style of bracket to use with the patient. Thus, as the landmarks 302 are placed, virtual brackets appear in the computer model on the labial surfaces of the teeth where the orthodontist desires to place the brackets. The orthodontist can move the bracket position depending on the type of forces the orthodontist wishes to create on teeth to correct the malocclusion. Because the brackets are individual objects and stored in memory, when they are placed on the surface of virtual teeth complete position information is known in three dimensions. As such, the brackets can be displayed either alone, or in conjunction with teeth, or hidden from view, by means of appropriate user specified commands on the user interface. For example, the screen display showing the target or current stage can have an icon indicating hide brackets, or display brackets, and activating the icon causes the brackets to be hid or displayed. The same is true for other virtual objects that exist independently of other objects, such as tooth models and the archwire.

With the teeth now separated into individual tooth objects, and the orthodontist can now view the current target stage, custom design a target situation for the patient, and design the appliance to treat the malocclusion.

Figure 3:
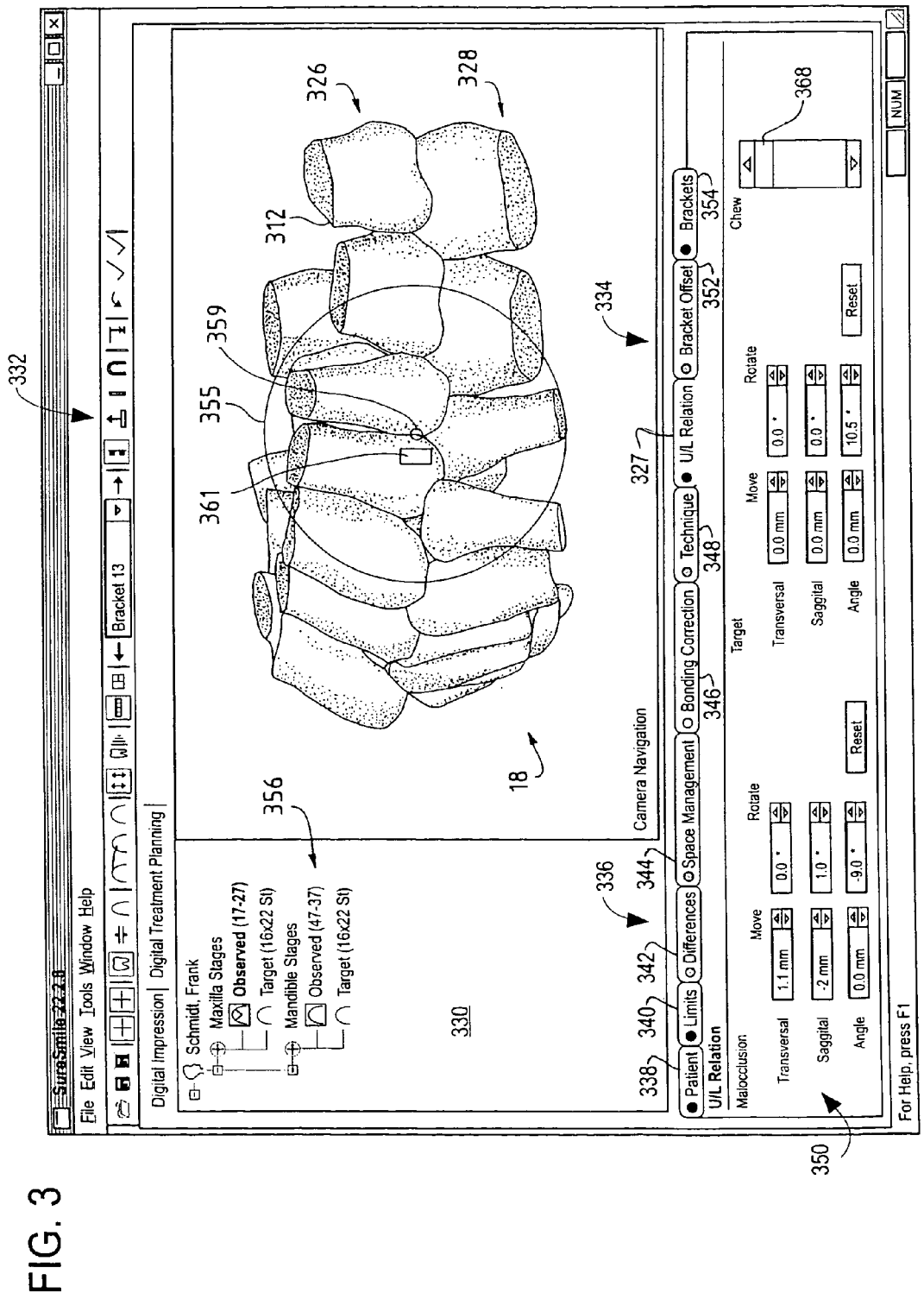
FIG. 3 is a screen shot from the treatment planning software showing a set of individual tooth objects representing the observed stage of a patient suffering from a malocclusion.

FIG. 3 is a screen shot showing a three-dimensional model 18 of a malocclusion, showing the teeth 312 in both the upper and lower arches 326 and 328, respectively. The screen 330 includes a row of icons 332 across the upper portion of the display, which are associated with various tools available to the user to view the dentition, virtual brackets, and current and target archforms. The lower portion 334 of the screen includes a set of tabs 336 that are accessed in various aspects of treatment planning. These tabs 336 include a patient tab 338, which accesses the screen of FIG. 3. A limits tab 340 allows a user to breakdown the tooth movement between observed and target stages into stages, such as 30 percent, 50 percent and 75 percent, and display the tooth positions for both arches at these positions. A differences tab 342 quantifies the differences (in terms of translation and rotation) between the observed and target stages for each tooth. The space management tab 344 permits the user to simulate extraction of one or more teeth and adjust the spacing between teeth in either arch. A bonding correction tab 346 allows for adjustment of tooth position to be realized via bonding corrections. The technique tab 348 allows the user to select a bracket prescription and default settings for bracket height (distance from bracket slot to incisal edge of tooth). The tab also displays the parameters for the bracket prescription chosen by the user. The upper/lower (U/L) relations tab 327, selected in the screen shot of FIG. 12, allows the user to modify the relation of the upper and lower jaws, by both translation in three axes (transversal, saggittal and vertical directions) and by rotation about these axes. The user manually enters values in the field 350 to change any parameter, and the change is immediately reflected in the view of the model of the dentition.

The tabs also include a bracket offset tab 352 that allows a user to reposition the bracket on a tooth and specifies numerical values for each bracket placement modification. A brackets tab 354 allows a user to enter information as to the type or manufacturer of brackets for each tooth in the both arches.

The screen shot of FIG. 3 also includes a region 356 that allows the user to navigate between views of the observed stage and views of the target stage. Here, the user has highlighted or selected both arches in the observed stage, so the screen display shows the model of the dentition in the current or observed stage.

Figure 4:
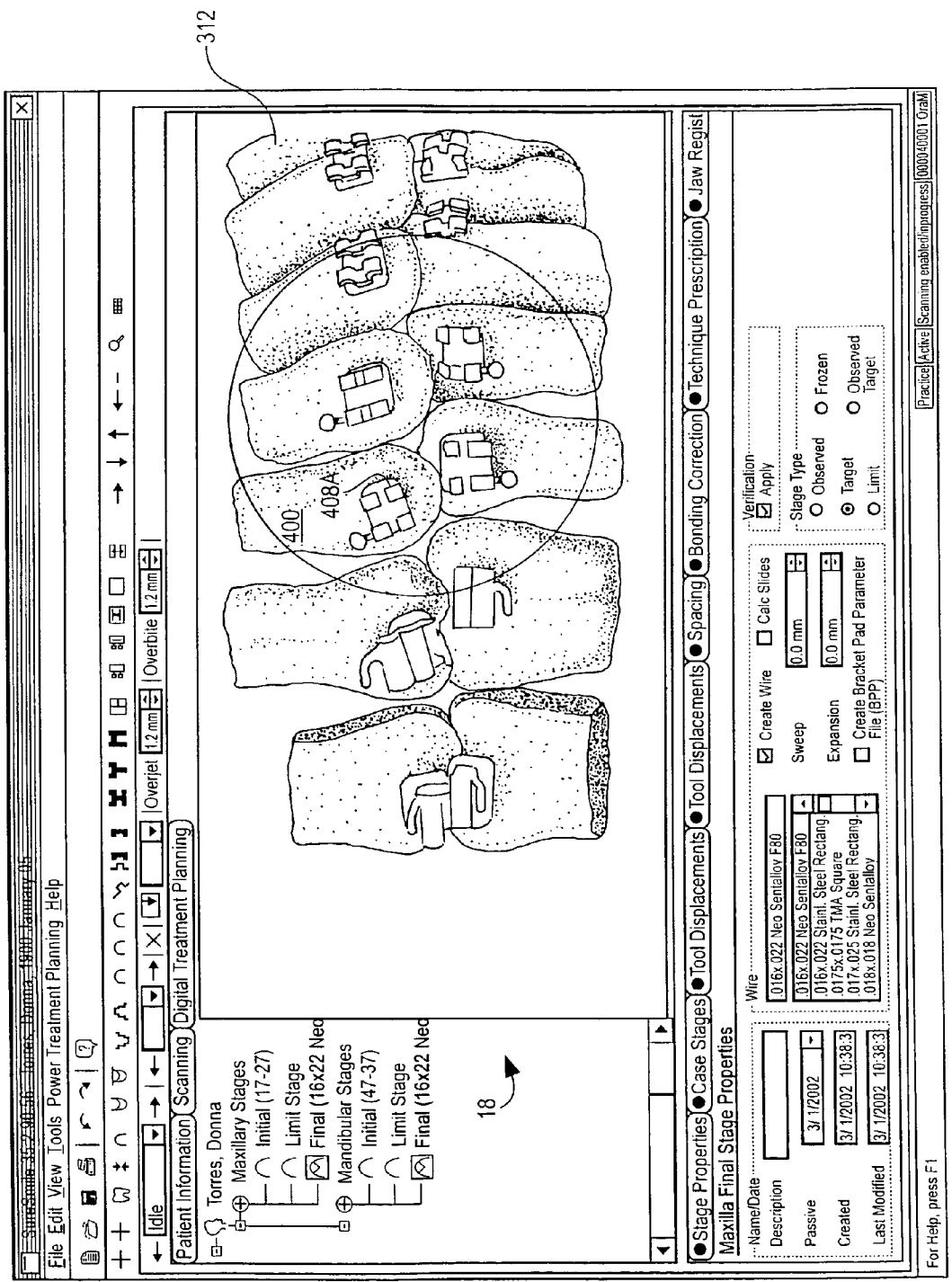
FIG. 4 is a screen shot showing the position of the teeth of the upper and lower arches in a proposed target or finish position, with virtual brackets placed on the virtual teeth.
Figure 5:
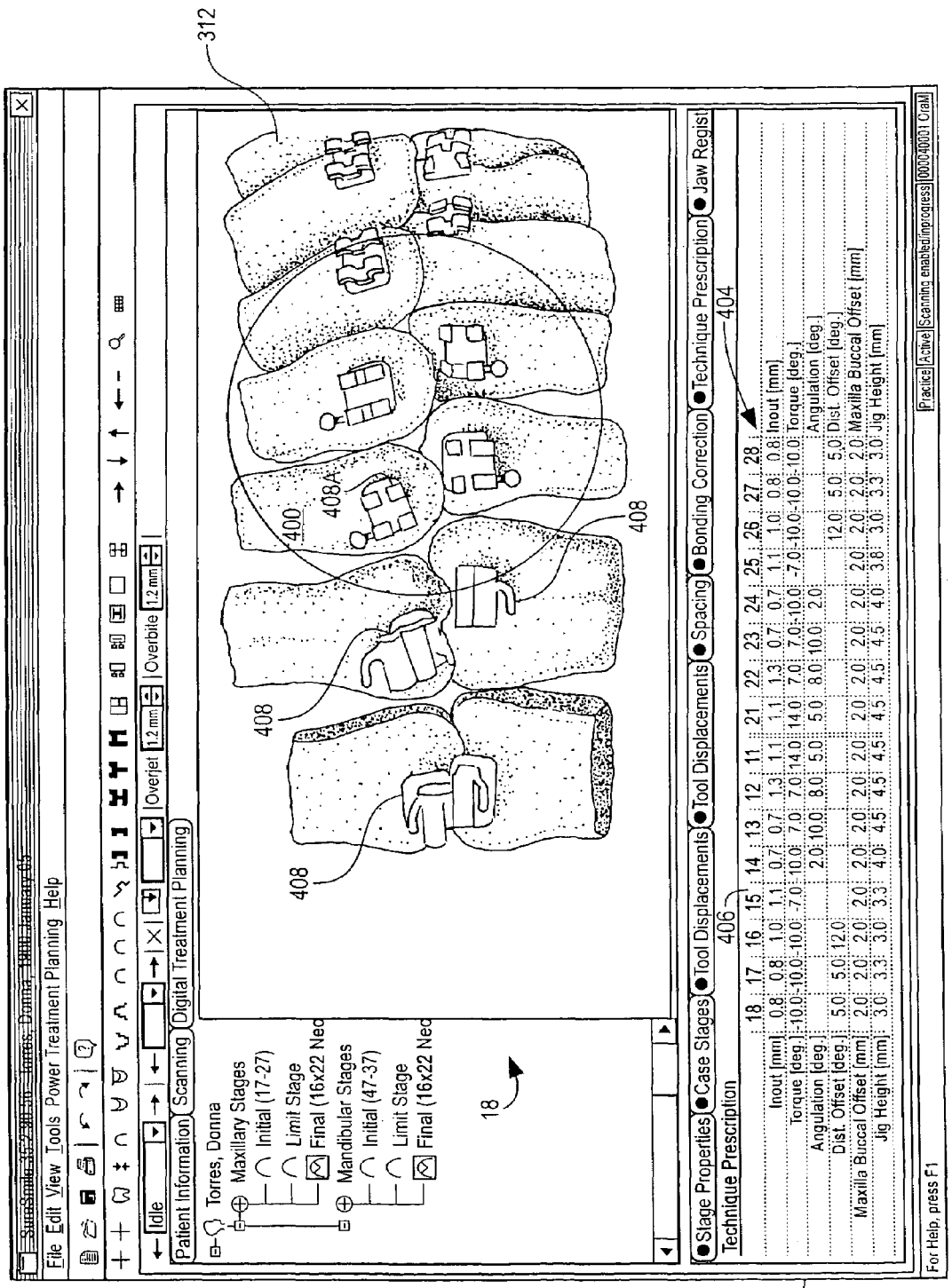
FIG. 5 is a screen shot similar to FIG. 4, with the user selecting a tab showing the prescription of the brackets placed on the teeth. The user can modify one or more elements of the bracket prescription simply by highlighting the relevant element and entering a new value. The change in prescription is immediately carried on the display in terms of movement of the selected tooth.

FIG. 4 is an illustration of a proposed tooth arrangement of the upper and lower arches of the patient. Brackets 408 are shown positioned on the teeth. A clinician then evaluates the proposed set up. In the present example, assume that the clinician is not satisfied with the position of the tooth 400 (tooth 15 in the treatment planning numbering system, 1 indicating the upper right quadrant and the 5th tooth over from the front incisor). Referring now to FIG. 5, the treatment planning software allows the user to select a techniques tab 402 which shows the individual bracket prescriptions for the brackets placed on the teeth. The techniques tab 402 includes a table 404 of all the brackets currently placed on the teeth, with the table indicating the relevant physical parameters of each bracket. The column 406 in the table is the prescription data for the bracket 408A on tooth 400 in FIGS. 4 and 5. As is shown in FIG. 5, the table includes prescription data for the bracket on the tooth: In—out in mm, torque in degrees, angulation in degrees, distal offset in degrees, maxilla buccal offset in mm, and jig height in mm.

It is important to note that the virtual brackets 408 illustrated in FIG. 5 are stored in a memory (such as the hard disk of the orthodontic workstation) and typically will be off-the shelf brackets with the prescription of the bracket and its three-dimensional shape stored in a file for the particular bracket. When the user starts a treatment planning session for the patient, the user is prompted to select on the user interface a bracket for each tooth from the library of available off-the-shelf brackets stored in the workstation. During treatment planning, the position of the brackets is displayed on the teeth as shown in FIGS. 4 and 5. However, the brackets are independent three-dimensional objects and their position on the teeth can be changed such as by clicking on a bracket to select the bracket and using navigation icons or the mouse to drag and reposition the bracket. The repositioning of the bracket affects the tooth finish position (assuming no change in the shape in the wire is made).

However, the treatment planning software provides the user the ability to actually change any of the entries in the bracket prescription in the table 404, to thereby effect a change in tooth position. For example, the user may wish to leave the position of the bracket 408A on the tooth 400 where it is but add an additional 3 degrees of torque to the prescription to provide for a better finish position for the tooth 400. The user is able to do this by clicking on the relevant column and row of the table 404 of FIG. 5 (such as the second row of column 406 to make a change in torque from −7 degrees to −10 degrees) and entering a new value for the prescription. The software takes the change in prescription into account by making an appropriate change in the position of the tooth. In this example, the torque of the tooth 400 is changed from −7 degrees to −10 degrees.

The change in the prescription of the bracket 408A from the prescription that is displayed on the screen initially, i.e., the prescription of an off-the-shelf bracket previously selected by the user, can result in two possible scenarios: first, that a customized bracket 408A is manufactured for the patient using the user-specified prescription. In the first scenario, the prescription and shape data for the bracket is exported to a milling machine or other fabrication device for fabrication of a customized bracket. Techniques for manufacture of a customized bracket are known in the art.

However, the requirement of using customized brackets adds additional costs and complexities to treatment of the patient and it is more preferable to use off-the-shelf brackets. In a second scenario, the new prescription data for bracket 408A entered by the user in the screen of FIG. 5 is compared with the prescription data of off-the shelf brackets stored in the library of virtual brackets and an off the shelf bracket is selected which comes closest to the prescription data for bracket 408A entered by the user. A variety of comparison algorithms can be readily derived that compare the prescription data, weight the differences between the prescription data entered by the user and the prescription data of the off-the-shelf brackets, compare the results from all the brackets in the library and select the appropriate bracket such that a "closest match" bracket is selected. Persons skilled in the art can readily develop the particular details of the algorithm. Once a "closest match" bracket is found, the bracket is displayed on the tooth and the user verifies tooth position. Any additional corrections to the tooth position can be achieved by bonding corrections (changing the location and orientation of the bracket on the tooth) or by making a change in the archwire.

Figure 6:
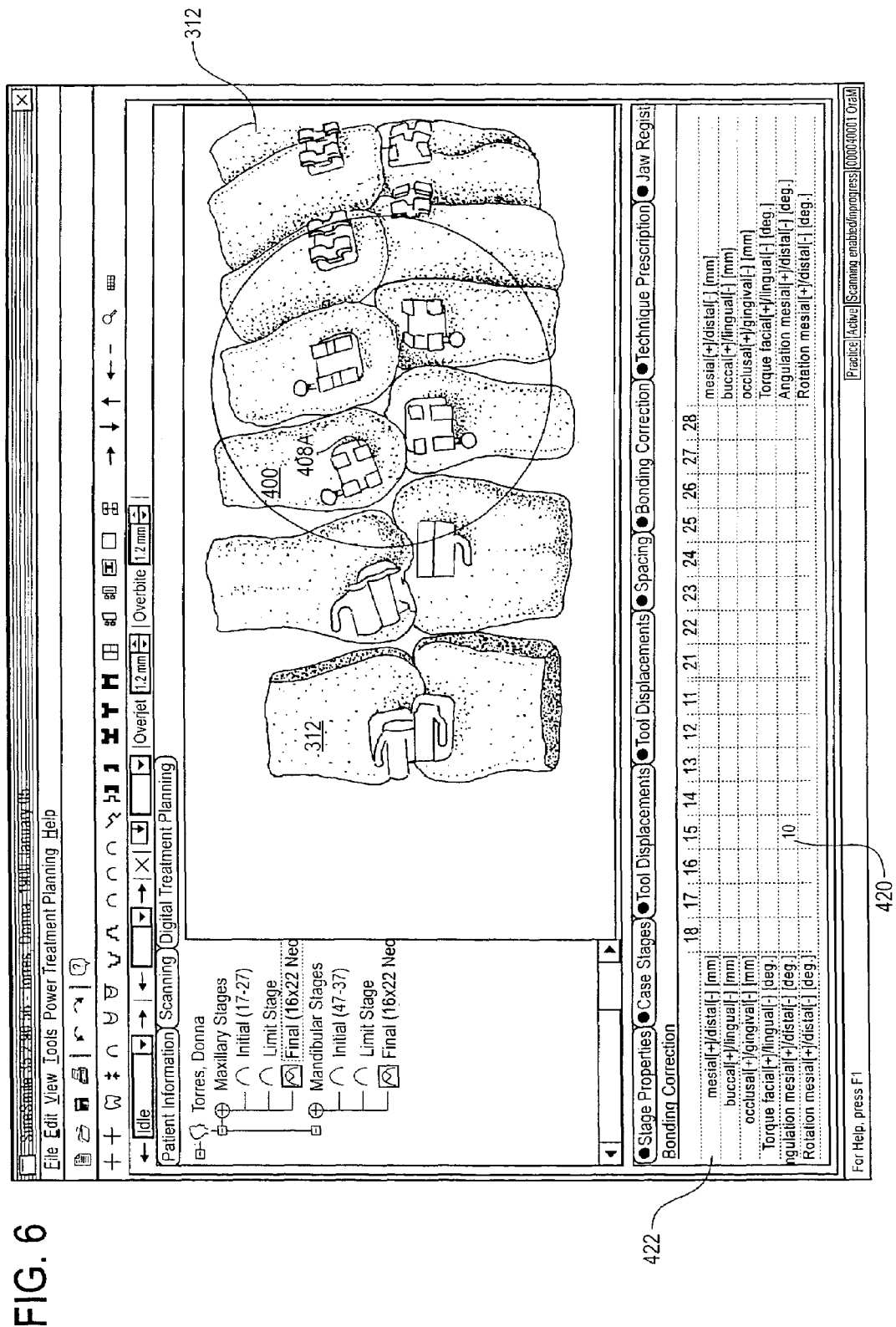
FIG. 6 is another screen show showing a 10 degree bonding correction applied to one of the brackets. The bonding correction affects the position of the bracket relative to the tooth in terms of a rotation relative to the tooth, and this affect results in a 10-degree tooth rotation in the tooth finish position. The same effect can be simulated by a 10-degree adjustment to the angulation parameter of the bracket prescription in FIG. 5.

An example of a bonding correction in shown in FIG. 6. The screen display shows the upper and lower arches of the teeth with the off-the shelf virtual brackets 408 resulting from the comparison step described previously placed on the teeth objects 312 in a proposed finish position. The user here wishes to make an additional mesial angulation bonding correction for the bracket 408A for tooth 400 (tooth 15 in the numbering convention used in the screen shot). The user makes this bonding correction by clicking on the appropriate box 420 in the bonding correction table 422 and typing in <10>. The position of tooth 400 immediately changes by an amount of 10 degrees, which can be verified by a comparison of the position of tooth 400 in FIG. 6 from the position in FIG. 5.

The process of using a stored library of virtual brackets has been described above for one tooth in one arch of the patient. Obviously, the technique can be extended to all the teeth in both arches. Further, while the technique has been shown for labial brackets, it can also be used for lingual brackets.

From the above discussion, and FIGS. 1, 4, 5 and 6, it will be appreciated that we have described an orthodontic workstation (e.g., workstation 28 of FIG. 1) which includes a central processing unit and a memory storing a set of virtual three-dimensional brackets 408. Each of the brackets 408 in the set has a unique prescription and a three-dimensional shape data. It will be noted that for any given patient more than one tooth may be fitted with an identical bracket.

As shown in FIGS. 4–6, the memory of the workstation further stores an interactive treatment planning program and a three-dimensional virtual model of the dentition of a patient. The treatment planning program selects a virtual three-dimensional bracket from the library for a virtual tooth in the three-dimensional virtual model of the dentition. This may occur for example by the user identifying for the treatment planning program which bracket they wish to use for the particular patient using a suitable entry type screen display, or as a result of selection of a closest fit bracket after the user has entered prescription information on a screen display such as shown in FIG. 5.

In the preferred embodiment the treatment planning program contains a set of instructions enabling a user of the treatment planning to place a virtual bracket on a virtual tooth in the three-dimensional virtual model of the dentition, such as described in conjunction with FIGS. 3 and 4 and modify the prescription for the bracket as shown in FIG. 5. The computer selects a new virtual bracket for the virtual tooth from the library of virtual brackets based on a comparison of the modification of the prescription and the prescription of the virtual brackets stored in the library.

In a preferred embodiment, the software allows a user to select a virtual bracket for the patient based upon a number of factors:

1) The aesthetics and material type. For example, the orthodontist selects a bracket from the library, places it on the virtual tooth, and shows the display to the patient and allows the patient see what they like, e.g., a ceramic bracket vs. a small size stainless steel bracket. If the patient is allergic to stainless steel a titanium bracket could be used.

2) Cost. It is possible to have two sets of brackets with equivalent prescriptions and the orthodontist or patient may elect the less expensive bracket. To obtain current price information, the software obtains periodic price updates from the manufacturer and this information is provided on the screen display along with the model of the bracket on the tooth.

3) Manufacturing tolerances. The bracket can be selected on the basis of how tight or close the manufacturing tolerances are, such as the tolerance in the slot height.

4) Fit of bonding base to tooth. The bracket selected for a given tooth can be based on how well the bonding base contour fits to the tooth surface. This can be done in two ways: first by running a clipping plane (i.e., cross-sectional view) at the interface of the bonding pad to the tooth and checking for the quality of fit subjectively. Alternatively, it is possible to use a contact algorithm to measure the distances between points on the surface of the tooth and the surface of the bonding pad (or vice versa) and if the surfaces are sufficiently close then selecting the bracket. Suitable contact algorithms for determining and displaying contact information is described in the patent application of Hans Imgrund, et al., entitled Three-dimensional Occlusal and Interproximal Contact Detection and Display Using Virtual Tooth Models, Ser. No. 10/137,495, filed on the same date of this application, the contents of which are incorporated by reference herein.

5) The force system. The bracket can be chosen based on the force system itself. The wider the bracket, the stiffer is the wire between the brackets. The orthodontist can set limits for forces and maintain the cross-section of the wire and change its stiffness by appropriately influencing the constraints, such as the dimensions of the bracket.

6) The bracket strength. It is possible to use finite element analysis to do a failure analysis for an orthodontic bracket. The same can be done to determine how well the bracket will hold on to the tooth. This analysis can also use the anticipated bracket bonding adhesive thickness and calculate the expected bonding strength from its adhesion strength, thickness, and surface area.

In one possible embodiment, these and possibly other factors are harnessed into a menu allowing for an optimization matrix defined by the individual patient's needs.

The concept of a virtual bracket library can be extended to other orthodontic appliances, such as a library of Herbst appliances, expansion devices, and virtual bands. The selection of the virtual bands for a patient can be done by using virtual libraries and checking the fit virtually rather than in the patient's mouth, saving time and patient inconvenience.

It will also be appreciated that we have described a method of planning treatment for an orthodontic patient, comprising the steps of:

a) obtaining a three-dimensional virtual model 18 of the dentition of the patient, e.g., from the scanning described in FIG. 1;

b) storing the virtual model of the dentition in a memory associated with an orthodontic treatment planning workstation 28 or 32;

c) providing, in the workstation 28 or 32, an interactive orthodontic treatment planning program enabling a user to 1) move the teeth in the virtual model to a proposed finish position and 2) place a virtual three-dimensional bracket on a virtual tooth in the virtual model 18;

d) providing, in the treatment planning program, an ability of a user to define the prescription of the virtual bracket, such as shown in FIG. 5 for bracket 408A; and e) automatically selecting an off-the-shelf bracket from a library of off-the-shelf brackets stored in or accessible to the computer.

In yet another aspect, and with reference to FIGS. 1, 3 and 6, we have described a method of planning treatment for an orthodontic patient, comprising the steps of:

a) obtaining a three-dimensional virtual model 18 of the dentition of said patient;

b) storing the virtual model 18 of the dentition in a memory associated with an orthodontic treatment planning workstation 28 or 32;

c) providing, in the workstation, an interactive orthodontic treatment planning program enabling a user to move the teeth in said virtual model to a proposed finish position, as shown in FIG. 5;

d) providing, in the memory, a library of virtual, three-dimensional brackets, a subset of the brackets being selected for individual teeth shown in FIGS. 5 and 6, for example, and e) providing in the treatment planning program, an ability of a user place the individual bracket (408A) on a virtual tooth 312 in the virtual model 18 and reposition the location of the virtual bracket 408 on the virtual tooth. For example, this is shown in FIG. 6 by providing a bonding correction tab in the treatment planning software which has tables that allow the user to enter numerical information as to the change they wish to make and the change is carried on the display. As another example; the user is provided the ability to select a given bracket by clicking the bracket with the mouse for the workstation and then repositioning the selected bracket by dragging the bracket with a mouse or using suitable navigation icons to rotate, translate or otherwise move the bracket relative to the tooth.

Paragraph 1:

The result of the treatment planning is the generation of a set of bracket placement positions and the display on the monitor of the shape of a customized orthodontic archwire to treat the malocclusion. Information as to the location of the brackets, the three-dimensional model of the malocclusion, the three dimensional model of the target situation, and the type of archwire to use are sent to the precision appliance center. A customized orthodontic archwire is manufactured in accordance with the bracket location and type and the target situation for the patient.

Paragraph 2:

Interactive, computer-based treatment monitoring is a significant advantage provided the treatment planning and appliance design aspects of the system described herein. Typically, when the patient comes into to the office during treatment, they will be scanned and a new digital model of the dentition is acquired. From this new model, differences can be monitored between the current situation and the original malocclusion, and differences between the current situation and the target situation or pre-defined limits or treatment stages as defined earlier. These differences can be quantified with precision. For example, a point on the tooth in the current model is selected, and the model of the tooth at the original malocclusion is overlaid on the screen. The superposition of the two teeth allows the user to view the change in position that has occurred. The measurement marker features described earlier allow the user to quantify precisely the amount of movement.

Paragraph 3:

Any deviations between the therapeutic result that is observed and the expected result can be captured precisely and at an early stage in treatment using the scanning and treatment planning features described herein, and corrected for. For example, the orthodontist may need to place additional bends in the archwire. Such additional bends can be performed by simulating the wire shape on the screen, displaying the wire only on the screen, and printing out the screen and using it as a template for bending the wire. The current situation could also be forwarded to the precision appliance center for manufacture of a new appliance. Of course, these monitoring and treatment corrections are applicable to any type of appliance selected for the patient.

Paragraph 4:

Basically, the position of the bracket slots, and the shape of the brackets, when the teeth are in a target situation, is information that is ultimately developed and stored byte treatment planning software. This position of the bracket slots and the shape of the slot (e.g., the length) is of course known in three dimensions. From the slot shape, it is possible to derive a three-dimensional set of line segments that represent the shape of an archwire passing through the bracket slots in the target situation, and calculating the optimal shape of bends that connect the bracket slots together. The positions of the straight sections and the bends are fed as an input file to a wire bending robot. The wire bending robot need only know the wire size, the shape and size of the slots, and the positions of the slots in the target situation. From this information, robot commands are generated to bend the archwire into the desired shape.

Paragraph 5:

The bending of the wire is based on slot data for bracket slots at described below, or based on some other suitable criteria as explained herein. The wire bending computer receives this slot data from the precision appliance center computer. The computer executes a bending program that processes the slot data into a set of points in three dimensional space and calculates movements of the moveable arm necessary to achieve the appropriate bends in the wire. The computer has a software interface to the robot controller, which translates position or movement signals for the robot arm into low level instructions for the robot controller. The robot controller executes a robot control program (adapted from the control program that comes with the robot) which causes the robot arm to move relative to the fixed gripper to bend and/or twist the wire. Where the archwire is a shape memory alloy, the wire heating power supply supplies current to the gripper fingers on the moveable arm and the gripper fingers on the fixed gripper to heat the wire while the wire is held in the bent condition, and/or during bending motion, to set the shape of the wire.

Paragraph 6:

The bending trajectory needs to be calculated for each bend. The bending trajectory is a number of positions of the moveable arm's gripper in relation to the fixed gripper, which connect the start position and the destination position of a bending movement. In general there are translational and rotational movement components from each bending trajectory position to the next.

Variations from the illustrated technique, methods and apparatus is contemplated without departure from the scope of the invention. The hardware aspects of the workstation and the potential for the workstation to perform other functions are not important. For example, the workstation implementing the treatment planning and virtual bracket library features described above could also function as a scanning node, a workstation also functioning as a billing workstation, a central server in a remote appliance manufacturing or appliance design facility, or it could be simply consist of a treatment planning workstation in an orthodontic clinic. This true scope is to be ascertained by reference to the appended claims.

We claim:

1. A workstation for orthodontic treatment planning, comprising:
   a central processing unit; and
   a memory, said memory storing a set of virtual three-dimensional brackets in the form of a library, each of said brackets in said set having a unique prescription and three-dimensional shape data,
   wherein said memory further stores an interactive treatment planning program and an original malocclusion three-dimensional virtual model of the dentition of a patient comprising a set of virtual teeth, and wherein said treatment planning program contains a set of instructions enabling an user of said treatment planning in:
   a) moving said set of virtual teeth to a proposed finish position;
   b) placing a plurality of virtual brackets selected from said library on a plurality of virtual teeth selected from said set of virtual teeth in said proposed finish position, wherein one virtual bracket is placed at an initial location selected by said user on the surface of one virtual tooth, and wherein each selected virtual bracket has a prescription;
   c) modifying said prescription of one or more of said virtual brackets selected in step b) and replacing each of said virtual brackets having said prescription modified with a new virtual bracket from said library wherein said new virtual bracket has a prescription that is the closest match to said modified prescription, and wherein the placement of said new virtual bracket on the corresponding virtual tooth is adjusted in accordance with the prescription of said new virtual bracket; and
   d) designing a customized archwire taking into account said virtual bracket prescriptions and said virtual bracket placements at the end of step c) where in said customized arch wire comprises line segments, bends and twists realized through translational and rotational movements;
   wherein said memory farther stores a new three-dimensional virtual model of the dentition of said patient acquired during monitoring of the treatment of said patient, and wherein said treatment planning program further contains a set of instructions enabling said user of said treatment planning in precisely quantifying the differences between said new three-dimensional virtual model and said original malocclusion, and the differences between said new three-dimensional virtual model and said proposed finish position; thereby enabling said user in adjusting the course of said treatment.

2. The workstation of claim 1, wherein said set of instructions selects said new virtual bracket based on a comparison of the modification of the prescription in step c) and the prescription of said virtual brackets stored in said library.

3. The workstation of claim 1, wherein said treatment planning program provides a display of said virtual tooth in said virtual model of the dentition and said virtual bracket placed on said tooth on the user interface of said workstation; and wherein said display further comprises a display of said prescription of said virtual bracket placed on said virtual tooth.

4. The workstation of claim 3, wherein said display enables a user to change a value of said prescription of said virtual bracket, and wherein said change in the value of said prescription causes a change in position of said virtual tooth relative to other teeth in said virtual model.

5. The workstation of claim 1, wherein said memory further stores three-dimensional objects comprising virtual models of orthodontic archwires derived from the cross-sectional shape and length of said archwire, and parameters as to the shape of the arch that said archwire is representing.

6. The workstation of claim 1, wherein in said initial location is identified by placing a landmark on the surface of said toot.

7. The workstation of claim 1, wherein in said placement of said new virtual bracket is further adjusted by a bonding correction.

8. A method of planning treatment for an orthodontic patient using an orthodontic treatment planning work station having a memory and an interactive treatment planning program, comprising the steps of:
   a) obtaining an original malocclusion three-dimensional virtual model of the dentition of said patient comprising a set of virtual teeth;
   b) storing said virtual model of the dentition in a said memory;
   c) storing a set of off-the-shelf virtual three-dimensional brackets in the form of a library in said memory, each of said brackets in said set having a unique prescription and three-dimensional shape data;
   d) moving said set of virtual teeth to a proposed finish position;
   e) placing a plurality of virtual brackets selected from said library on a plurality of virtual teeth selected from said set of virtual teeth in said proposed finish position, wherein one virtual bracket is placed at an initial location selected by said user on the surface of one virtual tooth, and wherein each selected virtual bracket has a prescription;
   f) modifying said prescription of one or more of said virtual brackets selected in step e) and replacing each of said virtual brackets having said prescription modified with a new virtual bracket from said library wherein said new virtual bracket has a prescription that is the closest match to said modified prescription, and wherein the placement of said new virtual bracket on the corresponding virtual tooth is adjusted in accordance with the prescription of said new virtual bracket;
   g) designing a customized archwire taking into account said virtual bracket prescriptions and said virtual bracket placements at the end of step f) where in said customized arch wire comprises line segments, bends and twists realized through translational and rotational movements;
   h) storing a new three-dimensional virtual model of the dentition of said patient acquired during monitoring of the treatment of said patient; and
   i) precisely quantifying the differences between said new three-dimensional virtual model and said original malocclusion, and the differences between said new three-dimensional virtual model and said proposed finish position; and thereby adjusting the course of said treatment.

9. The method of claim 8, wherein said interactive treatment planning program selects said new virtual bracket based on a comparison of the modification of the prescription in step f) and the prescription of said virtual brackets stored in said library.

10. The method of claim 8, wherein said treatment planning program provides a display of said virtual tooth in said virtual model of the dentition and said virtual bracket placed on said tooth on the user interface of said workstation; and wherein said display further comprises a display of the prescription of said virtual bracket placed on said tooth.

11. The method of claim 10, wherein said display enables a user to change a value of said prescription of said virtual bracket and wherein said change in the value of said prescription causes a change in position of said virtual tooth relative to other teeth in said virtual model.

12. The method of claim 8, wherein said memory further stores three-dimensional objects comprising virtual models of orthodontic archwires derived from the cross-sectional shape and length of said archwire, and parameters as to the shape of the arch that said archwire is representing.

13. The method of claim 8, wherein in said initial location is identified by placing a landmark on the surface of said tooth.

14. The method of claim 8, wherein in said placement of said new virtual bracket is further adjusted by a bonding correction.

15. The method of claim 8, wherein while placing a virtual bracket on a virtual tooth the collision avoidance algorithms are used to prevent the virtual bracket from entering the virtual tooth itself.

* * * * *